(12) United States Patent
Kovi et al.

(10) Patent No.: US 11,111,208 B2
(45) Date of Patent: Sep. 7, 2021

(54) PROCESS FOR THE PREPARATION OF SAFINAMIDE MESYLATE INTERMEDIATE

(71) Applicant: RK Pharma Solutions LLC, Piscataway, NJ (US)

(72) Inventors: Ravishanker Kovi, Monroe Township, NJ (US); Jayaraman Kannappan, Vadodara (IN); Rajesh A Patel, Vadodara (IN); Daxeshkumar Prakashbhai Patel, Vadodara (IN)

(73) Assignee: RK PHARMA SOLUTIONS LLC, Piscataway, NJ (US)

( * ) Notice: Subject to any disclaimer, the term of this patent is extended or adjusted under 35 U.S.C. 154(b) by 0 days.

(21) Appl. No.: 16/899,903

(22) Filed: Jun. 12, 2020

(65) Prior Publication Data

US 2021/0040031 A1 Feb. 11, 2021

(30) Foreign Application Priority Data

Jun. 17, 2019 (IN) .............................. 201921023977

(51) Int. Cl.
*C07C 231/12* (2006.01)
*C07C 45/63* (2006.01)
*C07C 303/32* (2006.01)
*C07C 45/71* (2006.01)
*C07C 47/575* (2006.01)
*C07C 237/06* (2006.01)

(52) U.S. Cl.
CPC ............ *C07C 231/12* (2013.01); *C07C 45/63* (2013.01); *C07C 45/71* (2013.01); *C07C 303/32* (2013.01); *C07C 47/575* (2013.01); *C07C 237/06* (2013.01)

(58) Field of Classification Search
None
See application file for complete search history.

(56) References Cited

U.S. PATENT DOCUMENTS

| 6,303,819 B1 * | 10/2001 | Pevarello .............. C07C 237/20 564/165 |
| 6,335,354 B2 | 1/2002 | Hogenkamp |
| 2010/0324141 A1 * | 12/2010 | Barbanti ............... C07C 231/12 514/567 |

FOREIGN PATENT DOCUMENTS

| WO | WO1990014334 A1 | 11/1991 |
| WO | WO2007147491 A1 | 12/2007 |
| WO | WO2009054964 A1 | 4/2009 |
| WO | WO2009074478 A1 | 6/2009 |
| WO | WO2011047767 A1 | 4/2011 |
| WO | WO-2019167085 A1 * | 9/2019 ........... C07C 231/24 |

* cited by examiner

*Primary Examiner* — Amy C Bonaparte
(74) *Attorney, Agent, or Firm* — Antonio Papageorgiou; Sharma Law Group PC

(57) ABSTRACT

The present application provides methods for the synthesis of intermediates in the synthesis of Safinamide or a pharmaceutically acceptable salt thereof herein Safinamide Mesylate, that is substantially free of impurities.

13 Claims, 1 Drawing Sheet

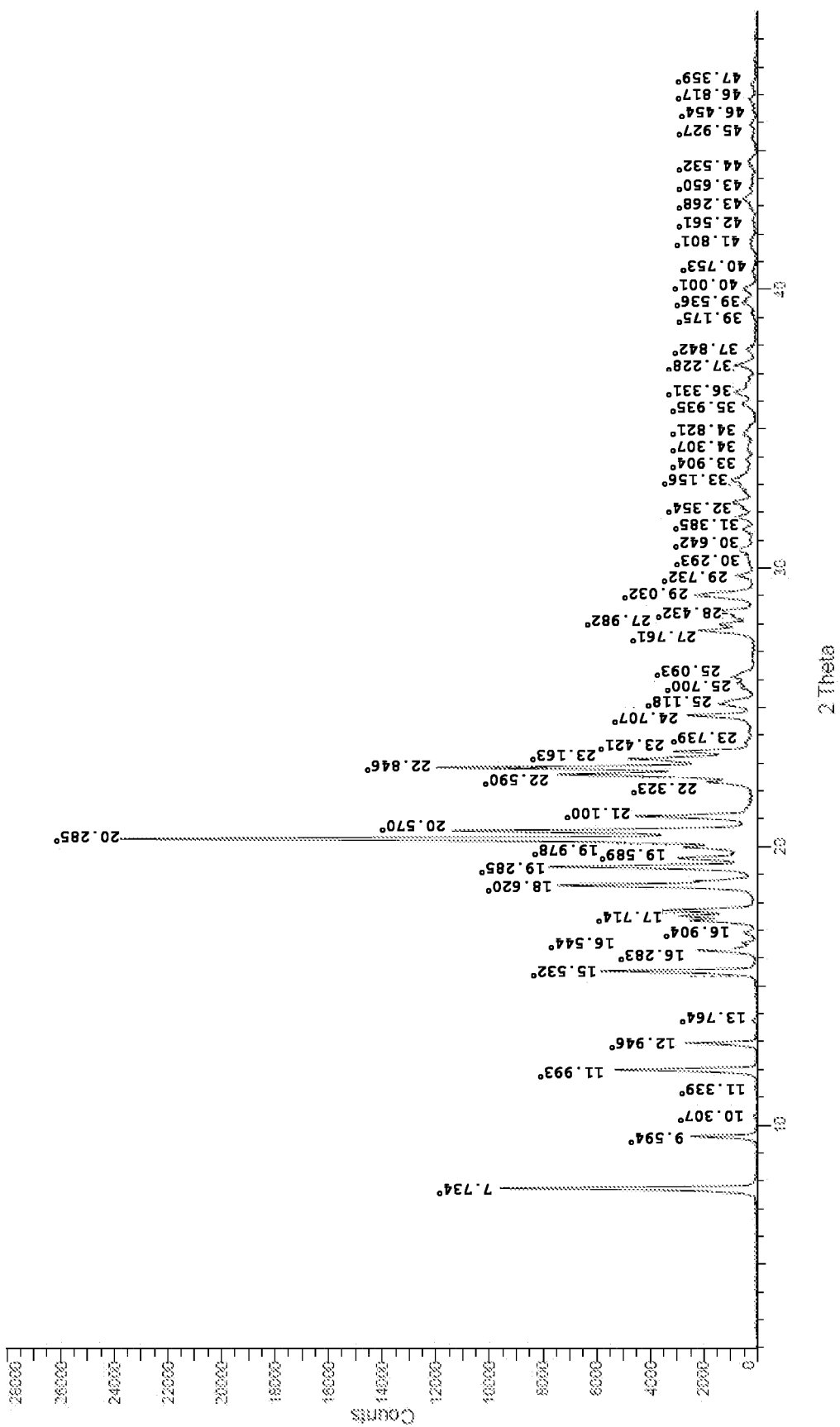

PROCESS FOR THE PREPARATION OF SAFINAMIDE MESYLATE INTERMEDIATE

FIELD OF THE INVENTION

The present application relates to Safinamide Mesylate of formula I. Specifically, the present application relates to improved processes for the preparation of a pure intermediate of Safinamide Mesylate. The present application also relates to the improvement in yield, with better purity, of Safinamide Mesylate.

BACKGROUND OF THE INVENTION

Safinamide mesylate (also called Xadago) is (S)-2-[[4-[(3-fluorophenyl) methoxy]phenyl]methyl]aminopropanamide methanesulfonate (1:1). Xadago tablets contain safinamide, which is a MAO-B inhibitor, as the mesylate salt. Safinamide mesylate has the following structural formula:

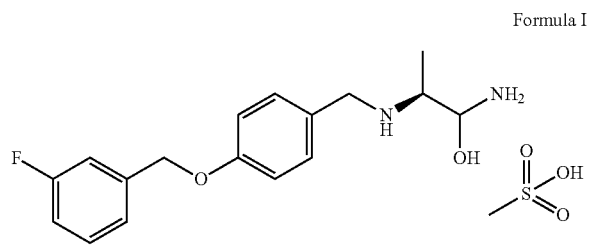

Formula I

The molecular formula of safinamide mesylate is $C_{17}H_{19}FN_2O_2 \cdot CH_4O_3S$ and its molecular weight is 398.45.

Safinamide mesylate is a white to off-white crystalline powder. Safinamide mesylate is freely soluble in water, methanol and dimethyl sulfoxide. Safinamide mesylate is sparingly soluble in ethanol and is practically insoluble in ethyl acetate. In aqueous buffers that span a pH range of 1.2 to 7.5, safinamide mesylate is highly soluble at pH 1.2 and 4.5, but shows low solubility (<0.4 mg/mL) at pH 6.8 and 7.5.

XADAGO is available as 50 mg and 100 mg film-coated tablets for oral administration. Each XADAGO tablet contains 65.88 mg or 131.76 mg of safinamide mesylate, equivalent to 50 mg or 100 mg, respectively, of safinamide free base. The tablets also contain the following inactive ingredients: colloidal silicon dioxide, crospovidone, hypromellose, iron oxide (red), magnesium stearate, microcrystalline cellulose, polyethylene glycol 6000, potassium aluminum silicate, and titanium dioxide.

Xadago is indicated as adjunctive treatment to levodopa/carbidopa in patients with Parkinson's disease (PD) experiencing "off" episodes. Xadago is a unique molecule with multiple mechanisms of action and a very high therapeutic index. It combines potent, selective, and reversible inhibition of MAO-B with blockade of voltage-dependent $Na^+$ and $Ca^{2+}$ channels and inhibition of glutamate release. Safinamide has neuroprotective and neurorescuing effects in MPTP-treated mice, in the rat kainic acid, and in the gerbil ischemia model.

Safinamide is discussed in WO 1990014334, which is incorporated herein by reference. The same application also discusses the synthesis and use of safinamide, such as anti-epileptic, anti-Parkinson, neuroprotective, antidepressant, antispastic and/or hypnotic agents.

WO 2007147491, which is also incorporated herein by reference, discusses high purity degree (S)-2-[4-(3-fluorobenzyloxy)-benzylamino]propanamide (safinamide) or (S)-2-[4-(2-fluorobenzyloxy)-benzylamino]propanamide (ralfinamide) or a salt thereof with a pharmaceutically acceptable acid with a content of the respective impurity (S)-2-[3-(3-fluorobenzyl)-4-(3-fluorobenzyloxy)-benzylamino]propanamide or (S)-2-[3-(2-fluorobenzyl)-4-(2-fluorobenzyloxy)-benzylamino]propanamide lower than 0.03% by weight. The process involves the formation of Schiff base intermediate to get highly pure safinamide mesylate.

WO 2009074478, which is also incorporated herein by reference, discusses the process for producing 2-[4-(3- or 2-fluorobenzyloxy)benzylamino]propanamide compound with a content of the respective impurity, (S)-2-[3-(3-fluorobenzyl)-4-(3-fluorobenzyloxy)-benzylamino]propanamide (IIa), (S)-2-[3-(2-fluorobenzyl)-4-(2-fluorobenzyloxy)-benzylamino]propanamide (IIb), lower than 0.03% by weight. This application also involves the formation Schiff base intermediate to give high pure safinamide mesylate.

WO 2009054964, which is also incorporated herein by reference, relates to novel alpha-aminoamide derivatives, their pharmaceutically acceptable salts, solvates, and hydrates thereof. The application also provides compositions comprising a compound and the use of such compositions in methods of treating diseases and conditions that are beneficially treated by administering an inhibitor of monoamine oxidase type B (MAO-B) and/or a sodium ($Na.sup.^+$) channel blocker, and/or a calcium ($Ca.sup.^{2+}$) channel modulator.

WO 2011047767, which is also incorporated herein by reference, discusses the anhydrate and crystalline polymorphic forms of Safinamide mesylate.

This art for the preparation Safinamide Mesylate of formula I suffer serious drawbacks. Such as more number of steps, higher industrial time with low yield and purities.

Step 1 involves a condensation reaction of 4-hydroxybenzaldehyde with 1-(chloromethyl)-3-fluorobenzene to get 4-((3-fluorobenzyl)oxy) benzaldehyde of formula V. 4-((3-fluorobenzyl)oxy) benzaldehyde (Formula V) on further subsequent reactions with S)-2-aminopropanamide and methane sulfonic acids gives Safinamide mesylate. Genotoxic impurity is formed during step (a), which carry over in the active pharmaceutical ingredient. Hence there is a continuous need to develop an improved and new process for the preparation of Safinamide intermediate that is 4-((3-fluorobenzyl)oxy) benzaldehyde (formula V) for commercial manufacturing with high yields and purity with minimum level of genotoxic impurity.

One or more embodiments of the present invention relate to intermediate preparation for manufacturing of safinamide crystalline modifications as well as their use in the treatment and/or prophylaxis of physiological and/or pathophysiological conditions.

Embodiments of the invention further relate to intermediates useful in the synthesis of pharmaceutically active compounds and methods of synthesizing safinamide mesylate.

The preparation of 4-((3-fluorobenzyl)oxy)benzaldehyde of formula V at high purity level in easily reproducible conditions is an essential requirement for the preparation of these important anti parkinson agents an industrial scale.

Accordingly, embodiments of the present invention provide improved industrial scale process for the preparation of Safinamide intermediate 4-((3-fluorobenzyl)oxy) benzaldehyde of formula V with better yield and purity.

SUMMARY OF THE INVENTION

In general, the present application provides methods for the synthesis of intermediates, in the synthesis of Safinamide or a pharmaceutically acceptable salt thereof herein Safinamide Mesylate. The application also provides intermediates that can be employed in the synthetic reactions described herein.

One object of certain embodiments of the invention is to develop the improved process for the preparation of Safinamide Mesylate intermediate 4-((3-fluorobenzyl)oxy) benzaldehyde of formula V comprising the steps of:

a) condensation reaction of 4-hydroxybenzaldehyde of formula II with 1-(chloromethyl)-3-fluorobenzene formula III by using potassium carbonate, potassium iodide in isopropyl alcohol to get crude 4-((3-fluorobenzyl)oxy)benzaldehyde of formula IV.

b) crude 4-((3-fluorobenzyl)oxy)benzaldehyde of formula IV is then treated with n-heptane to remove, preferably all, genotoxic impurity to afford pure 4-((3-fluorobenzyl)oxy) benzaldehyde of formula V.

A schematic representation of the improved process according to at least one embodiment is depicted below:

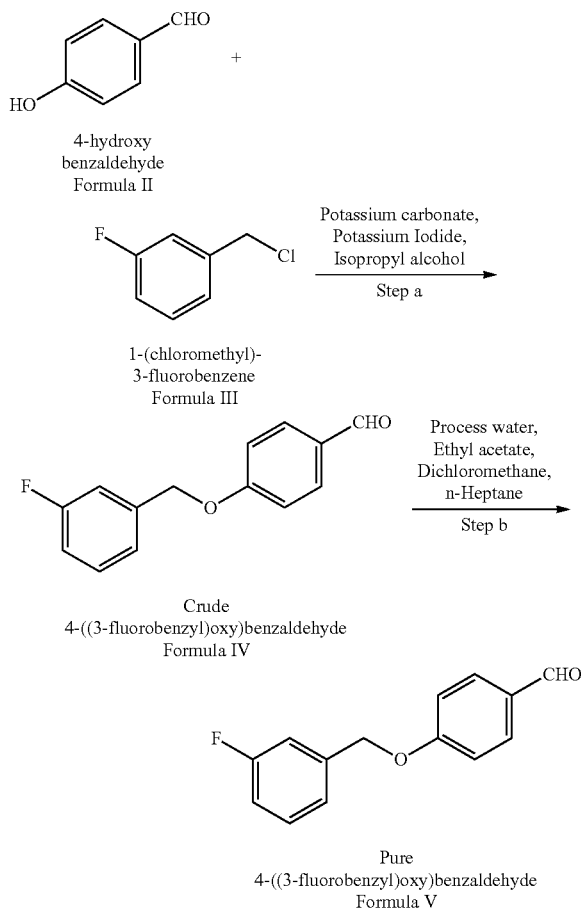

BRIEF DESCRIPTION OF THE DRAWINGS

The FIGURE is illustrative of a characteristic X-ray powder diffraction pattern of Safinamide mesylate.

DETAILED DESCRIPTION

Aspects in the preparation of Safinamide Mesylate are quality and production costs of the end product. Owing to regulatory requirements, high quality standards have to be met. Of interest in this context are purity and content of the active compound. Coupled to purity, it is in particular the spectrum of by-products that needs to be monitored. Minor components have to be toxicologically qualified and assessed. Accordingly, such components are listed in specifications and the maximum occurrence in the product is defined. For product safety, the by-product spectrum and the presence of individual contaminants are kept as low as possible to achieve the desire result.

U.S. Pat. No. 6,335,354, which is incorporated herein by reference discusses the process for the synthesis of Safinamide intermediate 4-((3-fluorobenzyl)oxy)benzaldehyde of formula V. The process involves the reaction of 4-hydroxybenzaldehyde with 1-(chloromethyl)-3-fluorobenzene by using potassium carbonate, potassium iodide in ethanol to get 4-((3-fluorobenzyl)oxy)benzaldehyde as yellow oil. Product formed here is carried to the next reaction without any purification. Genotoxic impurity is formed during this step, which may include:

1. 4-((4-fluorobenzyl)oxy) benzaldehyde,
2. 4-((2-fluorobenzyl)oxy) benzaldehyde,
3. 2-((3-fluorobenzyl)oxy) benzaldehyde,
4. 3-((3-fluorobenzyl)oxy) benzaldehyde, and
5. 3-(3-fluorobenzyl)-4((3-fluorobenzyl)oxy)benzaldehyde Thus there is a need for an improved process that ultimately improves the yield with minimum genotoxic impurity.

In a first embodiment, the present invention involves an improved process for the preparation of Safinamide Mesylate intermediate that includes the steps of:

a) condensation reaction of 4-hydroxybenzaldehyde of formula II with 1-(chloromethyl)-3-fluorobenzene of formula III by using potassium carbonate, potassium iodide in isopropyl alcohol to get crude 4-((3-fluorobenzyl)oxy)benzaldehyde of formula IV.

b) crude is then treated with n-heptane to remove all genotoxic impurity to afford pure 4-((3-fluorobenzyl)oxy) benzaldehyde of formula V.

Highly pure 4-((3-fluorobenzyl)oxy)benzaldehyde of formula V (Safinamide aldehyde) may then be treated with L-Alaninamide hydrochloride of formula VI in presence of sodium cyanoborohydride and methanol to get Safinamide of formula VII.

Safinamide of formula VII may then be treated with methane sulfonic acid in ethyl acetate to get pure Safinamide mesylate of formula I.

Schematic representation for synthesis of Safinamide mesylate is depicted below:

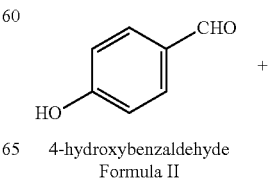

4-hydroxybenzaldehyde
Formula II

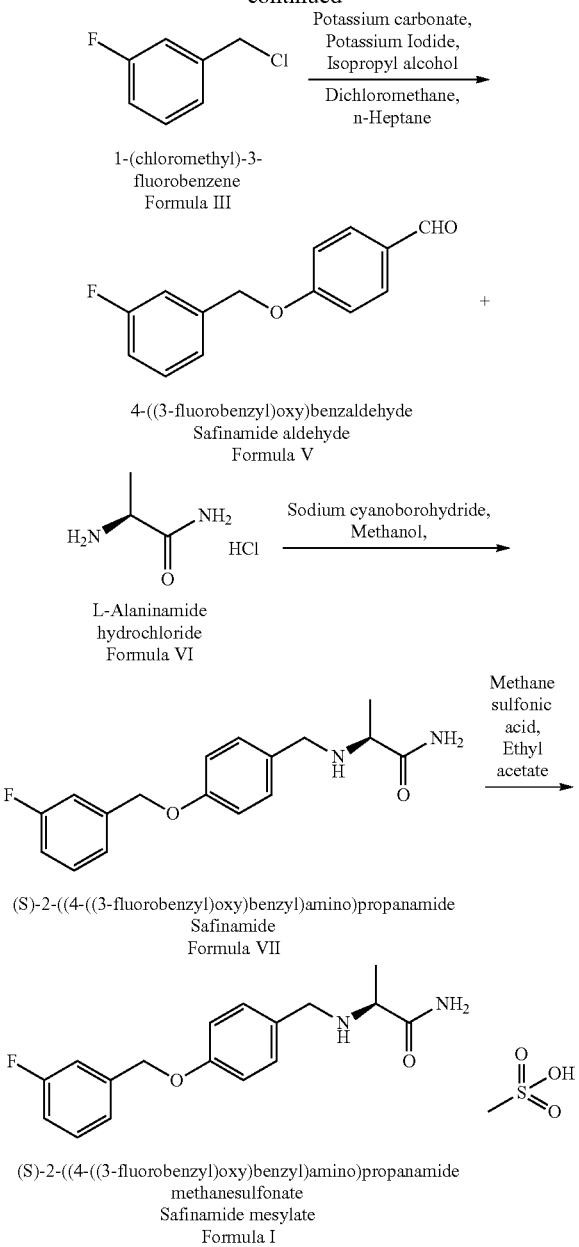

Condensation in step a may include: reaction of 4-hydroxybenzaldehyde with 1-(chloromethyl)-3-fluorobenzene by using base, catalyst in suitable solvent to get crude 4-((3-fluorobenzyl)oxy)benzaldehyde.

Suitable base includes but is not limited to sodium carbonate, sodium bicarbonate, potassium carbonate, sodium hydroxide, potassium hydroxide etc.

Suitable catalyst includes but is not limited to sodium iodide, potassium iodide Suitable solvents which can be used in step a for the preparation of compound II includes alcohols, such as methanol, ethanol, isopropanol, butanol and the like; nitriles, such as acetonitrile, propionitrile and the like; cyclic ether, such as tetrahydrofuran, furan, ethylene oxide, solvents like DMSO, DMF, DMA and the like; any mixtures of two or more thereof. Preferably, alcohol solvent is used, more preferably isopropanol.

A suitable temperature for the reaction of step a, may be between about 20° to about 120° C., preferably between about 40° C. to about 100° C., or preferably about 70° C. to about 90° C., or any other suitable temperatures. The reaction may be carried out for any desired time period ranging from about 30 minutes to about 24 hours or longer.

The isolation of crude intermediate may be induced by using conventional techniques known in the art. For example, useful techniques include but are not limited to concentrating, cooling, separation, stirring, shaking, combining with an anti-solvent, adding seed crystals, evaporation, flash evaporation, simple evaporation, rotational drying, or the like.

The crude that is obtained may carry a small proportion of occluded mother liquor containing a higher percentage of impurities and, if desired, the crude may be washed with a solvent to wash out the mother liquor. Evaporation as used herein refers to distilling of solvent almost completely at atmospheric pressure or under reduced pressure. Flash evaporation as used herein refers to distilling of solvent by using a technique includes but is not limited to tray drying, fluidized bed drying. The recovery of intermediate can be done by decantation, centrifugation, gravity filtration, suction filtration, and the like.

The resulting intermediate may be optionally further purified by using conventional technique known in the art. The techniques may include but not limited to treating the crude product into suitable solvent to get slurry. The recovery of pure intermediate can be done by decantation, centrifugation, gravity filtration, suction filtration, and the like. Drying can be carried out in a tray dryer, vacuum oven, air oven, cone vacuum dryer, rotary vacuum dryer, fluidized bed dryer, spin flash dryer, flash dryer, or the like. The drying can be carried out at temperatures of less than about 60° C., less than about 40° C., less than about 30° C., less than about 20° C., or any other suitable temperatures; at atmospheric pressure or under a reduced pressure; as long as the crystalline intermediate is not degraded in its quality. The drying can be carried out for any desired times until the required product quality is achieved. Suitable time for drying can vary from few minutes to several hours for example from about 30 minutes to about 24 or more hours.

Safinamide mesylate obtained by this process is crystalline in nature. XRD for Safinamide mesylate is depicted in the FIGURE.

The Safinamide Mesylate intermediate synthesize by this route have advantageous properties selected from at least one of: chemical purity, stability—such as storage stability, stability to dehydration, stability to polymorphic conversion, flowability, solubility, morphology or crystal habit, low hygroscopicity and low content of residual solvents.

Certain specific aspects and embodiments of the present application will be explained in more detail with reference to the following examples, which are provided only for purposes of illustration and should not be construed as limiting the scope of the present application in any manner.

EXPERIMENTAL SECTION

Preparation of 4-((3-fluorobenzyl)oxy)benzaldehyde 4-hydroxybenzaldehyde (10 gm) was dissolved in isopropyl alcohol (40 ml) at room temperature. Potassium carbonate (11.32 gm.) and potassium iodide (0.68 gm.) was added into reaction mass. 3-Fluorobenzyl chloride (10.41 mL) was further added into above reaction mass. The reaction mass was then heated to get 75° C. to 85° C. and stirred for about six hours at the same temperature. After completion of reaction, reaction mass was diluted with water and then extracted with ethyl acetate. Organic layer was evaporated under vacuum to get crude intermediate.

Crude product was then treated with heptane to remove genotoxic impurity and get 4-((3-fluorobenzyl)oxy)benzaldehyde. 4-((3-fluorobenzyl)oxy)benzaldehyde was then dissolved dichloromethane and treated with potassium carbonate. Finally crude was treated with heptane to get pure 4-((3-fluorobenzyl)oxy)benzaldehyde (Safinamide aldehyde) with the following characteristics:

Practical Yield: 8.7 gm
Purity by HPLC: 99.92%

Preparation of Safinamide

First, RBF L-Alaninamide hydrochloride (6.493 gm.) was dissolved in methanol (50 ml) at room temperature. The reaction mass was heated to between about 45° C. to about 55° C. Sodium Cyanoborohydride (4.094 gm) was charged into the above reaction mass at about 45° C. to 55° C. Separately, RBF 4-((3-fluorobenzyl)oxy)benzaldehyde (Safinamide aldehyde) (10 gm) was dissolved in methanol (30 ml). This reaction mass was added slowly into first the RBF at about 45° C. to 55° C. The reaction mass was then stirred for 6 hours at about 45° C. to 55° C.

After completion of the reaction, the reaction mass was diluted with water (50 ml) and Dichloromethane (50 ml) into reaction mass at about 20° C. to about 30° C. Potassium carbonate solution [by using potassium carbonate (5 gm) in process water (50 ml)] was charged into the reaction mass at about 20° C. to 30° C. After stirring for about 30 minutes, layers were separated. Organic layer was distilled out under vacuum below about 50° C. Residue were than dissolved in ethyl acetate (35 ml) and refluxed at about 75° C. to 85° C. The reaction mass was cooled to room temperature (RT), filtered, and washed with ethyl acetate (10 ml). Wet material was then dried under vacuum oven to get Safinamide with a Practical Yield: 9.6 gm.

Preparation of Safinamide Mesylate

Safinamide was dissolved in ethyl acetate at room temperature. The Reaction mass was refluxed at about 75° C. to 85° C. Slowly, methane sulfonic acid solution was added into reaction mass at about 75° C. to 85° C. The reaction mixture was then stirred for about 30 minutes at about 75° C. to 85° C. The reaction mixture was then cooled to about 45° C. to 55° C. and filtered. The material was dried under vacuum 60° C. to get Safinamide mesylate with the following characteristics: Practical Yield: 11.4 gm; Purity by HPLC: 99.98%

While the foregoing has been described in some detail for purposes of clarity and understanding, it will be appreciated by one skilled in the art, from a reading of the disclosure, that various changes in form and detail can be made without departing from the true scope of the invention.

What is claimed is:

1. A method for the preparation of a compound, comprising:
   a condensation reaction of 4-hydroxybenzaldehyde of formula II with 1-(chloromethyl)-3-fluorobenzene of formula III, using potassium carbonate, and potassium iodide in a solvent, and removing the solvent after completion of the condensation reaction, therewith producing crude 4-((3-fluorobenzyl)oxy)benzaldehyde of formula IV;
   treating the crude with n-heptane to remove genotoxic impurities;
   dissolving the treated crude in dichloromethane and treating the solution with potassium carbonate; and
   treating the treated solution with n-heptane to afford 4-((3-fluorobenzyl)oxy)benzaldehyde of formula V having a purity greater than 99%.

2. The method of claim 1, wherein the solvent comprises an alcohol selected from the group consisting of methanol, ethanol, isopropanol, and butanol.

3. The method of claim 1, wherein the solvent comprises a nitrile selected from the group consisting of acetonitrile and propionitrile.

4. The method of claim 1, wherein the solvent comprises a cyclic ether selected from the group consisting of tetrahydrofuran, furan, and ethylene oxide.

5. The method of claim 1, wherein the solvent comprises at least one of DMSO (dimethyl Sulfoxide), DMF (dimethylformamide), and DMA (dimethylacetamide).

6. The method of claim 1, wherein the resulting 4-((3-fluorobenzyl)oxy)benzaldehyde of formula V has a purity of greater than 99.9%.

7. The method of claim 1, comprising using the pure 4-((3-fluorobenzyl)oxy)benzaldehyde of formula V for the synthesis of safinamide mesylate of formula I.

8. The method of claim 7, wherein the resulting safinamide mesylate of formula I is crystalline.

9. The method of claim 7, wherein the resulting safinamide mesylate of formula I has a purity of greater than 99% and is prepared by reacting pure 4-((3-fluorobenzyl)oxy) benzaldehyde of formula V with L-alaninamide hydrochloride in the presence of methanol and sodium cyanoborohydride to get safinamide and further reacting the safinamide with methane sulfonic acid using ethyl acetate as solvent to obtain safinamide mesylate.

10. The method of claim 9, wherein the resulting safinamide mesylate of formula I has a purity of greater than 99.9%.

11. The method of claim 1, wherein the resulting crude formula IV, before the first treatment with n-heptane, has a purity of greater than 99%.

12. The method of claim 1, wherein the resulting crude formula IV, before the first treatment with n-heptane, has a purity of greater than 99.9%.

13. The method of claim 1, wherein removing the solvent comprises evaporating the solvent under vacuum.

* * * * *